US007899683B2

(12) United States Patent
Schoenberg et al.

(10) Patent No.: US 7,899,683 B2
(45) Date of Patent: Mar. 1, 2011

(54) MEDICAL INFORMATION SYSTEM

(75) Inventors: Ido Schoenberg, Tel Aviv (IL); Phyllis Gotlib, Tel Aviv (IL); Roy Schoenberg, Tel Aviv (IL); Hagai Sherlin, Natanya (IL)

(73) Assignee: I.M.D. Soft Ltd., Needham, MA (US)

( * ) Notice: Subject to any disclaimer, the term of this patent is extended or adjusted under 35 U.S.C. 154(b) by 1323 days.

(21) Appl. No.: 10/985,950

(22) Filed: Nov. 12, 2004

(65) Prior Publication Data
US 2005/0125256 A1 Jun. 9, 2005

Related U.S. Application Data

(62) Division of application No. 09/946,274, filed on Sep. 5, 2001, now Pat. No. 7,831,450, which is a division of application No. 09/341,065, filed as application No. PCT/IB97/01606 on Dec. 29, 1997, now Pat. No. 6,322,502.

(60) Provisional application No. 60/034,111, filed on Dec. 30, 1996.

(51) Int. Cl.
G06Q 50/00 (2006.01)
(52) U.S. Cl. .................. 705/2; 705/3; 600/300
(58) Field of Classification Search .................. 705/2–3; 600/300
See application file for complete search history.

(56) References Cited

U.S. PATENT DOCUMENTS

| 3,646,606 A | 2/1972 | Buxton et al. |
| 4,489,387 A | 12/1984 | Lamb et al. |
| 4,709,331 A | 11/1987 | Barkett et al. |
| 4,719,338 A | 1/1988 | Avery et al. |
| 4,731,725 A | 3/1988 | Suto et al. |
| 4,736,322 A | 4/1988 | Clifford |

(Continued)

FOREIGN PATENT DOCUMENTS

WO    WO 98/29790    7/1998

(Continued)

OTHER PUBLICATIONS

Oliver, Suzanne, Take two aspirin; The computer will call in the morning. Forbes. New York: Mar. 14, 1994. vol. 153, Iss. 6; p. 110. 2 pgs.*

(Continued)

*Primary Examiner* — R. D Rines
(74) *Attorney, Agent, or Firm* — Fish & Richardson P.C.

(57) ABSTRACT

A medical information system receives patient data and information from various sources and displays such information in a variety of formats for use by members of a medical team in a hospital, clinic, or office. The system receives patient information from doctors, pharmacists, patient monitoring equipment, testing laboratories, and/or computer databases. Access to selected subsets of patient information is provided by user selection of specific data sets identified by job function selection icons. A member of the medical team can record observations about a patient using key words and phrases which can be supplemented with additional text for customized notation. Multiple types of patient data are selectively displayed simultaneously, and to multiple remote users. The system can access stored data according to user-specified formulae to compute a score or metric which reflects a relationship between various factors, each factor being weighted appropriately according to its significance as defined in the formula. A user can selectively display data in graphic form by "clicking" on a row of tabular data in a tabular region of the display and "dragging and dropping" that row to a graphic display region of the display.

18 Claims, 5 Drawing Sheets

U.S. PATENT DOCUMENTS

| | | | |
|---|---|---|---|
| 4,807,170 A | 2/1989 | Kulli et al. | |
| 4,835,372 A * | 5/1989 | Gombrich et al. | 235/375 |
| 4,838,275 A | 6/1989 | Lee | |
| 4,852,570 A | 8/1989 | Levine | |
| 4,878,175 A | 10/1989 | Norden-Paul et al. | |
| 5,065,315 A | 11/1991 | Garcia | |
| 5,199,439 A | 4/1993 | Zimmerman et al. | |
| 5,255,187 A | 10/1993 | Sorensen | |
| 5,262,944 A | 11/1993 | Weisner et al. | |
| 5,301,105 A * | 4/1994 | Cummings, Jr. | 705/2 |
| 5,305,205 A | 4/1994 | Weber et al. | |
| 5,307,263 A | 4/1994 | Brown | |
| 5,321,800 A | 6/1994 | Lesser | |
| 5,335,346 A | 8/1994 | Fabbio | |
| 5,361,202 A | 11/1994 | Doue | |
| 5,398,300 A * | 3/1995 | Levey | 706/16 |
| 5,404,292 A | 4/1995 | Hendrickson | |
| 5,447,164 A | 9/1995 | Shaya et al. | |
| 5,482,050 A | 1/1996 | Smokoff et al. | |
| 5,544,649 A | 8/1996 | David et al. | |
| 5,572,422 A | 11/1996 | Nematbakhsh et al. | |
| 5,574,828 A | 11/1996 | Hayward et al. | |
| 5,592,945 A | 1/1997 | Fiedler | |
| 5,594,638 A * | 1/1997 | Iliff | 705/3 |
| 5,619,991 A | 4/1997 | Sloane | |
| 5,630,664 A | 5/1997 | Farrelly | |
| 5,682,526 A | 10/1997 | Smokoff et al. | |
| 5,687,717 A | 11/1997 | Halpern et al. | |
| 5,704,350 A | 1/1998 | Williams, III | |
| 5,713,350 A * | 2/1998 | Yokota et al. | 600/300 |
| 5,715,451 A | 2/1998 | Marlin | |
| 5,722,999 A | 3/1998 | Snell | |
| 5,724,580 A | 3/1998 | Levin et al. | |
| 5,729,479 A | 3/1998 | Golan | |
| 5,752,621 A | 5/1998 | Passamante | |
| 5,772,585 A | 6/1998 | Levin et al. | |
| 5,772,601 A | 6/1998 | Oka et al. | |
| 5,781,442 A * | 7/1998 | Engleson et al. | 700/214 |
| 5,794,208 A | 8/1998 | Goltra | |
| 5,801,755 A | 9/1998 | Echerer | |
| 5,822,544 A * | 10/1998 | Chaco et al. | 705/2 |
| 5,823,948 A | 10/1998 | Ross, Jr. et al. | |
| 5,830,150 A | 11/1998 | Palmer et al. | |
| 5,832,450 A | 11/1998 | Myers et al. | |
| 5,839,438 A | 11/1998 | Graettinger et al. | |
| 5,842,976 A | 12/1998 | Williamson | |
| 5,842,978 A | 12/1998 | Levy | |
| 5,845,255 A * | 12/1998 | Mayaud | 705/3 |
| 5,860,918 A | 1/1999 | Schradi et al. | |
| 5,867,821 A * | 2/1999 | Ballantyne et al. | 705/2 |
| 5,868,669 A | 2/1999 | Iliff | |
| 5,912,656 A | 6/1999 | Tham et al. | |
| 5,921,920 A | 7/1999 | Marshall et al. | |
| 5,924,074 A | 7/1999 | Evans | |
| 5,940,815 A | 8/1999 | Maeda et al. | |
| 5,942,986 A * | 8/1999 | Shabot et al. | 340/7.29 |
| 5,956,689 A | 9/1999 | Everhart, III | |
| 5,970,463 A | 10/1999 | Cave et al. | |
| 5,997,476 A | 12/1999 | Brown | |
| 6,024,699 A | 2/2000 | Surwit et al. | |
| 6,047,259 A | 4/2000 | Campbell et al. | |
| 6,061,657 A | 5/2000 | Whiting-O'Keefe | |
| 6,101,478 A | 8/2000 | Brown | |
| 6,112,182 A | 8/2000 | Akers et al. | |
| 6,206,829 B1 | 3/2001 | Iliff | |
| 6,230,142 B1 | 5/2001 | Benigno et al. | |
| 6,233,581 B1 | 5/2001 | Rambaud et al. | |
| 6,283,761 B1 * | 9/2001 | Joao | 434/236 |
| 6,322,502 B1 * | 11/2001 | Schoenberg et al. | 600/300 |
| 6,363,393 B1 | 3/2002 | Ribitky | |
| 6,364,834 B1 | 4/2002 | Reuss et al. | |
| 6,381,576 B1 | 4/2002 | Gilbert | |
| 6,385,589 B1 | 5/2002 | Trusheim et al. | |
| 6,413,224 B1 | 7/2002 | Ogura et al. | |
| 6,463,320 B1 | 10/2002 | Xue et al. | |
| 6,658,276 B2 | 12/2003 | Kianl et al. | |
| 6,700,028 B2 | 3/2004 | Dryoff | |
| 6,748,353 B1 | 6/2004 | Iliff | |
| 6,804,558 B2 | 10/2004 | Haller et al. | |
| 6,804,656 B1 * | 10/2004 | Rosenfeld et al. | 705/3 |
| 6,941,271 B1 | 9/2005 | Soong | |
| 7,039,878 B2 | 5/2006 | Auer et al. | |
| 7,374,535 B2 | 5/2008 | Schoenberg et al. | |
| 2002/0087355 A1 | 7/2002 | Rowlandson | |
| 2002/0099273 A1 | 7/2002 | Bocionek et al. | |
| 2002/0173988 A1 | 11/2002 | Dang | |
| 2002/0177758 A1 | 11/2002 | Schoenberg et al. | |
| 2002/0177759 A1 | 11/2002 | Schoenberg et al. | |
| 2002/0187483 A1 | 12/2002 | Hoffman et al. | |
| 2003/0036687 A1 | 2/2003 | Schoenberg | |
| 2003/0163351 A1 | 8/2003 | Brown et al. | |
| 2004/0111296 A1 | 6/2004 | Rosenfeld | |
| 2004/0111297 A1 | 6/2004 | Schoenberg | |
| 2004/0111298 A1 | 6/2004 | Schoenberg | |
| 2004/0111622 A1 | 6/2004 | Schoenberg | |
| 2004/0152952 A1 | 8/2004 | Gotlib et al. | |
| 2004/0153343 A1 | 8/2004 | Gotlib et al. | |
| 2004/0225629 A1 | 11/2004 | Eder | |
| 2005/0125256 A1 | 6/2005 | Schoenberg et al. | |
| 2005/0256815 A1 | 11/2005 | Reeve et al. | |
| 2006/0004610 A1 | 1/2006 | David | |
| 2008/0208618 A1 | 8/2008 | Schoenberg et al. | |

FOREIGN PATENT DOCUMENTS

| | | |
|---|---|---|
| WO | WO 99/13766 | 3/1999 |
| WO | WO 00/79466 | 12/2000 |
| WO | WO 00/79466 A2 | 12/2000 |
| WO | WO 2005/067675 | 7/2005 |
| WO | WO 2005/067675 A2 | 7/2005 |

OTHER PUBLICATIONS

PTO Decision on Re-examination for Patent No. 6,804,656.

Visicu/Cerner Complaint for Patent No. 6,804,656.

Shabot, Michael M. and LoBue, Mark. *Real-Time Wireless Decision Support Alerts on a Palmtop PDA*, Journal of the American Medical Informatics Association. Nineteenth Annual Symposium on Computer Applications in Medical Care (Oct. 28-Nov. 1, 1995), pp. 174-177.

Hosseinzadeh, Abolfazl, "A Rule-Based System for Vital Sign Monitoring in Intensive Care", Department of Electrical Engineering, McGill University, Montreal; Nov. 1993.

Aukburg, S.J. et al., "Automation of Physiological Data Presentation and Alarms in the Post Anesthesia Care Unit." In Symposium on Computer Applications in Medical Care, Nov. 5-8, 1989, Washington, DC; pp. 580-582.

Benis, A. M. et al., "Improved Detection of Adverse Cardiovascular Trends with the Use of a Two-Variable Computer Alarm" *Critical Care Medicine*, vol. 8, No. 2, Jun. 1980: 341-344.

Bierman, M. I. et al., "Pulse Oximetry in the Postoperative Care of Cardiac Surgical Patients; A Randomized Controlled Trial." *Chest*, vol. 102, No. 5, Nov. 1992: 1367-1370.

Bradshaw, K. E., "Computerized Alerting System Warns of Life-Threatening Events." In Symposium on Computer Application in Medical Care, Oct. 25-26, 1986, Washington, DC; pp. 403-409.

Chizeck, H. J., "Modelling, Simulation and Control in a Data Rich Environment." In Symposium on Computer Applications in Medical Care, Oct. 25-26, 1986, Washington, DC; pp. 65-69.

Coiera, E., "Intelligent Monitoring and Control of Dynamic Physiological Systems." *Artificial Intelligence in Medicine*, vol. 5, 1993: pp. 1-8.

Colvin, J. R. et al., "Microcomputer-Controlled Administration of Vasodilators Following Cardiac Surgery: Technical Considerations." *J. Cardiothoracic Anesthesia*, vol. 3, No. 1, Feb. 1989: pp. 10-15.

Coplin, W. M. et al., "Accuracy of Continuous Jugular Bulb Oximetry in the Intensive Care Unit." Neurosurgy, vol. 42, No. 3, Mar. 1998: 533-540.

Crew, A. D. et al., "Preliminary Clinical Trials of a Computer-Based Cardiac Arrest Alarm." Intensive Care Med, vol. 17, 1991: 359-364.

Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Guedes de Oliveira, P. et al., "The Role of Computer Based Techniques in Patient Monitoring: Technical Note." *Acta Neuorchir*, vol. 55, 1992 (Suppl.): 18-20.

Hahnel, J. et al., "Can a Clinician Predict the Technical Equipment a Patient will Need During Intensive Care Unit Treatment? An Approach to Standardize and Redesign the Intensive Care Unit Workstation." *J. Clinical Monitoring*, vol. 8, No. 1, Jan. 1992: 1-6.

Hall, G. L. & P.B. Colditz, "Continuous Physiological Monitoring: An Integrated System for Use in Neonatal Intensive Care." *Australian Physical & Engineering Sciences in Medicine*, vol. 18, No. 3, 1995; 139-142.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Irazurta, Jose, "Monitoring in Pediatric Intensive Care." *Indian J. Pediatrics*, vol. 60, 1993: 55-65.

Jans, R. et al., "A Low Cost ECG Central Station for Intensive Care." *Australian Physical & Engineering Sciences in Medicine*, vol. 13, No. 1, 1990: 31-35.

Jastremski, M. et al., "A Model for Technology Assessment as Applied to Closed Loop Infusion Systems." *Critical Care Medicine*, vol. 23, No. 10, Oct. 1995: 1745-1755.

Klass, M. A. & E. Y. Cheng, "Early Response to Pulse Oximetry Alarms with Telemetry." *J. Clinical Monitoring*, vol. 10, No. 3, May 1994: 178-180.

Kohane, I. S. et al., "Hypothesis-Driven Data Abstraction with Trend Templates." In Symposium on Computer Applications in Medical Care, Oct. 30-Nov. 3, 1993, Washington, DC; pp. 444-448.

Koski, E. M. J. et al., "A Knowledge-Based Alarm System for Monitoring Cardiac Operated Patients—Assessment of Clinical Performance." *International J. Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International J. Clinical Monitoring and Computing*, vol. 8, 1992: 289-293.

Laffel, G. et al., "Using Control Charts to Analyze Serial Patient-Related Data." *Quality Management in Health Care*, vol. 3, No. 1, Fall 1994: 70-77.

L'Estrange, P. R. et al., "A Microcomputer System for Physiological Data Collection and Analysis." *Australian Dental Journal*, vol. 38, No. 5, Oct. 1993: 400-405.

M. de Beer, N. A. et al., "Clinical Evaluation of a Method for Automatic Detection and Removal of Artifacts in Auditory Evoked Potential Monitoring." *J. Clinical Monitoring*, vol. 11, No. 6, Nov. 1995: 381-391.

Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.

Makivirta, A. & E. M. J. Koski, "Alarm-Inducing Variability in Cardiac Postoperative Data and the Effects of Prealarm Delay." Critical Care Medicine, vol. 8, No. 6, May 1994: 153-162.

Martin; J. F., "Closed-Loop Control of Arterial Pressure During Cardiac Surgery." *J. Clinical Monitoring*, vol. 8, No. 3, Jul. 1992: 252-253.

Meyer, C., "Visions of Tomorrow's ICU." *American J. Nursing*, Apr. 1993: 27-31.

Nenov, V. I. et al., "Computer Applications in the Intensive Care Unit." *Neurosurgery Clinics of North America*, vol. 5, No. 4, Oct. 1994: 811-827.

Nobel, J. J., "Physiologic Monitoring Systems, Acute Care." *Pediatric Emergency Care*, vol. 8, No. 4, Aug. 1992: 235-237.

Orr, J. A. & Westenskow, D. R., "A Breathing Circuit Alarm System Based on Neural Networks." *J. Clinical Monitoring*, vol. 10, No. 2, Mar. 1994: 101-109.

Pappert, D. et al., "Preliminary Evaluation of a New Continuous Intra-Arterial Blood Gas Monitoring Device." *Acta Anaesthesiologica Scandinavica*, Suppl. 107, vol. 39, 1995: 67-70.

Rampil, I. J., "Intelligent Detection of Artifact." *The Automated Anesthesia Record and Alarm Systems*, Chapter 17, 1987: 175-190.

Runciman, W. B. et al., "The Pulse Oximeter: Applications and Limitations—An Analysis of 2000 Incident Reports." *Anaesthesia and Intensive Care*, vol. 21, No. 5, Oct. 2003: 543-550.

Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.

Sanklecha, M., "The Pulse Oximeter." *Indian J. Pediatrics*, vol. 60, No. 3, 1993: 469-470.

Schnapp, L. M. & N. J. Cohen, "Pulse Oximetry; Uses and Abuses." *Chest*, vol. 98, No. 5, Nov. 1990: 1244-1250.

Simpson, R. L., "Automating the ICU: Facing the Realities." *Nursing Management*, vol. 23, No. 3, Mar. 1992: 24-26.

Sittig, D. F. & M. Factor, "Physiological Trend Detection and Artifact Rejection: A Parallel Implementation of a Multi-State Kalman Filtering Algorithm." In Symposium on Computer Applications in Medical Care, Nov. 5-8, 1989, Washington, DC; pp. 569-574.

Stoodley, K. D. C. et al., "Problems in the Development of a Computerized Ward Monitoring System for a Pediatric Intensive Care Unit." *International J. Clinical Monitoring and Computing*, vol. 8, 1992: 281-287.

Sukavaara, T. et al., "A Knowledge-based Alarm System for Monitoring Cardiac Operated Patients—Technical Construction and Evaluation." *International J. Clinical Monitoring and Computing*, vol. 10, 1993: 117-126.

Szaflarski, N. L., "Emerging Technology in Critical Care: Continuous Intra-Arterial Blood Gas Monitoring." *American J. Critical Care*, vol. 5, No. 1, Jan. 1996: 55-65.

Uckun, S., "Intelligent Systems in Patient Monitoring and Therapy Management." *International J. Clinical Monitoring and Computing*, vol. 11, 1994: 241-253.

Webb, R. K., "Medical Decision Making and Decision Analysis." *Anesthesia and Intensive Care*, vol. 16, No. 1, Feb. 1988: 107-109.

Yien, H. et al., "Spectral Analysis of Systemic Arterial Pressure and Heart Rate Signals as a Prognostic Tool for the Prediction of Patient Outcome in the Intensive Care Unit." *Critical Care Medicine*, vol. 25, No. 2, 1997: 258-266.

Tsien, Christine L. and James Fackler, "Poor Prognosis for Existing Monitors in the Intensive Care Unit" *Critical Care Medicine*, vol. 25, No. 4, 1997: 614-619.

Tsien, Christine L... "Reducing False Alarms in the Intensive Care Unit: A Systematic Comparison of Four Algorithms" Proceedings *AMIA* Symposium, 1997. pp. 9-14 (unnumbered).

Tsien, Christine L. "Reducing False Alarms in the Intensive Care Unit: A Systematic Comparison of Four Algorithms" Proceedings Annual *AMIA* Fall Symposium (Paper on CD-ROM) 1997.

Tsien, Christine L. "Reducing False Alarms in the Intensive Care Unit: A Systematic Comparison of Four Algorithms" Proceedings Annual *AMIA* Fall Symposium (1997), p. 894.

Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R. Cohen, and M. R. Berthold, Eds.; Springer-Verlag, London, UK; pp. 111-121.

Zhao, Ruilin, "A Model-Based Expert System for Interpretation of Hemodynamic Data from ICU Patients." Department of Electrical Engineering and Computer Science, Massachusetts Institute of Technology; May 18, 1997 (pp. 1-121).

Jamzad et al. "A human friendly reporting and database system for brain PET analysis" Annals of Nuclear Medicine 10(1):99-104, 1996.

Litt et al. "Graphical representation of medical information in the visual chart" Proceedings, 1994 IEEE Seventh Symposium on Computer-based Medical Systems, pp. 252-257, Jun. 11-12, 1994.

Nossister. Using Excel 5 for Windows (The User Friendly Reference), Copyright 1995, by Que Corporation.

Laurenson, R.C., "Computer Software 'Article of Manufacture' Patents," *JPTOS*,:811-824 (1995) Previously appeared in *Computer Law Reporter*, 21(6):965-974 (1995).

Miksch, Silvia, "Artificial Intelligence for Design Support: Needs Possibilities, and Limitations in ICU," 10*th* Postgraduate Course in Critical Care Medicine APICE '95, Springer, 1995.

Lee, Ho Sung et al., "Remote Patient Monitoring Service through World-Wide Web" Proceedings—19th International Conference—IEEE/EMBS Oct. 30-Nov. 2, Chicago, IL. USA; pp. 928-931.

Grundy, Betty L. et al., "Telemedicine in Critical Care: An Experiment in Health Care Delivery" JACEP, vol. 6, No. 10., Oct. 1977; pp. 439-444.

Lee, Ho Sung et al. "Remote Patient Monitoring Service Through World-Wide Web." *Proceedings from the 19th International Conference of IEEE/EMBS*, Chicago, IL US (Nov. 2, 1997), pp. 928-931.

Li, et al. "A World Wide Web Telemedicine System." *SPIE*, vol. 2711 (Feb. 13, 1996), pp. 427-439.

Avila, Lorene S. and M. Michael Shabot, "Keys to the Successful Implementation of an ICU Patient Data Management System," *International Journal of Clinical Monitoring and Computing*, vol. 5, 1988, pp. 15-25.

Berg, et al. "Remote Critical Care Consultation: Telehealth projection of clinical specialty expertise". Tripler Army Medical Center, Honolulu.

Capuano, Terry Ann et al. Remote Telemetry, Nursing Management, Vo.26, No. 7, Jul. 1995, p. 26.

Chu, Wesley W. et al. "A Medical Digital Library to Support Scenario and User-Tailored Information Retrieval." *Transactions on Information Technology in Biomedicine*, vol. 4, No. 2, Jun. 2000, pp. 97-107.

Clayton, P.D. et al., "Data Driven Interpretation of Laboratory Results in the Context of a Medical Decision Support System" *Clinical Biochemistry, Principles-Methods, Applications 2*, Data Presentation Interpretation (Eds. H. Keller and Ch. Trendelenburg), Walter deGruyter, Berlin—New York, 1989; Chapter 3.7; pp. 367-380.

Doctors use 'remote control' to monitor ICU patients, CNN.com. technology>computing, Aug. 21, 2000, http://www.cnn.com/2000/TECH/computing/08/21/icu..t_t/.

East, Thomas D. et al., "Computers in Critical Care" *Critical Care Nursing Clinics of North America*, vol. 7, No. 2, Jun. 1995; pp. 203-216.

Gardner, Reed M. et al., "Computers in the Intensive Care Unit: A Match Meant to Be!" *Textbook of Critical Care*, Chapter 196, Third Edition, W.B. Saunders Company, 1995; pp. 1757-1770.

Gardner, Reed M., "Computerized Management of Intensive Care Patients" *Images, Signals and Devices*, vol. 3, No. 1, 1986; pp. 36-51.

Henkind, S.J., et al., "A Clinical Alarm System Using Techniques from Artificial Intelligence and Fuzzy Set Theory," *Approximate Reasoning in Intelligent Systems, Decision and Control*, Pergamon Press, 1987, pp. 91-104.

Henkind, Steven et al. "Intensive Care Unit Monitoring Using a Real-Time Expert System," *Computers in Cardiology*, Sep. 18-21, Salt Lake City, Utah, 1994, pp. 7-12.

Heterington. "High tech meets high touch: telemedicine's contribution to patient wellness". Nursing Administration Quarterly, 22(3), Spring 1998.

Ingenerf, Josef. "Telemedicine and Terminology: Different Needs of Context Information." *Transactions on Information Technology in Biomedicine*, vol. 3, No. 2, Jun. 1999, pp. 92-100.

Janofsky, Michael. "Finding Value in Intensive Care, from Afar," The New York Times on the Web, Jul. 27, 1999, www.Visicu.com/companynews/0799_nytimes.htm.

Johnson, Bob et al., *Discern—An Integrated Prospective Decision Support System*, Symposium on Computer Applications in Medical Care. A Conference of the American Medical Informatics Associated, Nov. 5-19, 1994, Washington, D.C. p. 969.

Kaplan, Simon M. et al. Designing Support for Remote Intensive-Care Telehealth Using the Locales Framework, ACM, 1997, 99.173-184.

Kimura, Michio et al. "MERIT-9: a patient information exchange guideline using MML, HL7, and DICOM." International Journal of Medical Informatics, vol. 51, No. 1, Jul. 1998, pp. 59-68.

Kleinholz, Lutz et al. "Supporting Cooperative Medicine: The Bermed Project." *IEEE Multimedia*, vol. 1, No. 4, Dec. 1994, pp. 44-53.

Kontaxis, K.M. et al. "Using XML and Controlled Vocabularies to Achieve Unambiguous Knowledge Acquistion From Multiple Hetereogeneous Medical Data Sources." *Information Technology Applications in Biomedicine*, 4*th* International IEEE EMBS Special Topic Conference on Apr. 24-26, 2003, pp. 161-164.

Leyerle, Beverley J. et al., "The PDMS as a Focal Point for Distributed Patient Data." *International Journal of Clinical Monitoring and Computing*, vol. 5, 1988. pp. 155-161.

Mabry, Susan L. et al., Integrated Medical Analysis System, Proceedings of the 1997 Winter Simlation Conference, 1997, pp. 1167-1168.

McDonald, CJ, "Protocol-Based Computer Reminders, the Quality of Care and the Non-Perfectibility of Man," *The New England Journal of Medicine*, vol. 295, No. 24, Abstract only, Dec. 9, 1976, Retrieved online from: Science Library.

Microsoft Press Computer Dictionary, Third Edition, 1997, p. 430.

Microsoft Support Document 236963 describing the functionality of the Windows 95 OS.

Nenov, Valeriy et al. Remote Access to Neurosurgical ICU Physiological Data using the World Wide Web, Health Care in the Information Age, 1996, pp. 242-249.

Oliver, Suzanne, "Take Two Aspirin; The Computer will Call in the Morning." Forbes, Mar. 14, 1994. pp. 110-111.

Palley, N. A., et al. "Programming in the Medical Real-Time Environment." *AFIPS Conference Proceedings*, vol. 37, *Fall Joint Computer Conference*, Nov. 17-19, 1970, Houston Texas. pp. 589-598.

Perednia, Douglas A. Telemedine Technology and Clinical Applications, JAMA, vol. 6, Feb. 8, 1995, p. 483.

Reddy, Dr. Ramana & Dr. V. "Juggy" Jagannathan, "Phase 1 Quarterly Report, Apr. 1-Jun. 30, 1997" *Secure Collaboration for Technology for Rural Clinical Telemedicine*, Funded by the National Library of Medicine, Copyright © 1999 West Virginia University; Retrieved from Internet, pp. 1-5.

Reddy, Dr. Ramana & Dr. V. "Juggy" Jagannathan, "Phase 1 Quarterly Report, Jan. 1-Mar. 1, 1997" *Secure Collaboration for Technology for Rural Clinical Telemedicine*, Funded by the National Library of Medicine, Copyright © 1999 West Virginia University; Retrieved from Internet, pp. 1-5.

Reddy, Dr. Ramana & Dr. V. "Juggy" Jagannathan, "Phase 1 Quarterly Report, Sep. 1-Dec. 1, 1996" *Secure Collaboration for Technology for Rural Clinical Telemedicine*, Funded by the National Library of Medicine, Copyright © 1999 West Virginia University; Retrieved from Internet, pp. 1-5.

Reddy, Dr. Ramana & Dr. V. "Juggy" Jagannathan, "Project Summary; Telemedicine Team" *Secure Collaboration for Technology for Rural Clinical Telemedicine*, Funded by the National Library of Medicine, Copyright © 1999 West Virginia University; Retrieved from Internet, pp. 1-12.

Remote Monitoring of ICU Patients Lowers Mortality Rates, Complications, Johns Hopkins News release, Mar. 20, 2001, http://www.newswise.com/areticles/2001/3/ICU.JTM.html.

Rind, David M., et al., "Effect of Computer-Based Alerts on the Treatment and Outcomes of Hospitalized Patients," *Archives of Internal Medicine*, Vo. 154, Jul. 11, 1994, pp. 1511-1517.

Rosenfeld, M.D., Brian A. FCCM, FCCP, et al., Intensive care unit telemedicine: Alternate paradigm for providing continuous intensivist care, Critical Care Medicine, vol. 28, No. 12, 2000 p. 3925.

Stewart. "Patenting of Software—Proposed Guidelines and the Magic Dividing Line that disappeared". JPTOS, pp. 681-698, Sep. 1995.

Tsien, Christine L., "TrendFinder: Automated Detection of Alarmable Trends", Department of Electrical Engineering and Computer Science, Massachusetts Institute of Technology, Massachusetts; Jun. 2000.

Weil, Max H., "Use of Automated Techniques in the Management of the Critically Ill," *Hospital Information Systems*, Marcel Dekker, Inc., 1972, 333-381.

Transaction History (PTO Website), for U.S. Appl. No. 09/946,421, dated May 29, 2009.

Transaction History (PTO Website), for U.S. Appl. No. 09/946,304, dated May 29, 2009.

Transaction History (PTO Website), for U.S. Appl. No. 09/946,274, dated May 29, 2009.

Transaction History (PTO Website), for U.S. Appl. No. 09/341,065, dated May 29, 2009.

Transaction History (PTO Website), for U.S. Appl. No. 90/007,927, dated May 29, 2009.
Transaction History (PTO Website), for U.S. Appl. No. 11/474,017, dated May 29, 2009.
Transaction History (PTO Website), for U.S. Appl. No. 10/355,527, dated May 29, 2009.
Transaction History (PTO Website), for U.S. Appl. No. 11/031,125, dated May 29, 2009.
Transaction History (PTO Website), for U.S. Appl. No. 09/443,072, dated May 29, 2009.
Transaction History (PTO Website), for U.S. Appl. No. 90/007,377, dated May 29, 2009.
Transaction History (PTO Website), for U.S. Appl. No. 90/008,276, dated May 29, 2009.
Transaction History (PTO Website), for U.S. Appl. No. 10/355,435, dated May 29, 2009.
International Searching Authority, Notification of Transmittal of the International Search Report and the Written Opinion of the International Searching Authority, or the Declaration for Application No. PCT/IB05/00646, dated Nov. 13, 2007, 9 pages.
Supplementary European Search Report for Application No. EP05708735, dated Nov. 13, 2008, 4 pages.
Non-final Office Action issued in U.S. Appl. No. 11/474,017, dated Mar. 31, 2010, 35 pages.
Jury Verdict in *Cerner Corporation* v. *Visicu, Inc.*, Civil Action No. 04-1033 (W.D. Mo., Judge Gary A. Fenner), filed Dec. 8, 2009, 5 pages.
"Vital Signs," http://en.wikipedia.org/wiki/Vital-signs (accessed on Jun. 9, 2010), 5 pages.
Non-final Office Action issued in U.S. Appl. No. 09/946,304, dated May 18, 2010, 15 pages.

* cited by examiner

FIG. 2A

MEDICAL INFORMATION SYSTEM

RELATED APPLICATION

This application is a divisional of U.S. patent application Ser. No. 09/946,274 filed on Sep. 5, 2001 now U.S. Pat. No. 7,831,450, which is a divisional of U.S. patent application Ser. No. 09/341,065 filed on Jun. 29, 1999 and issued as U.S. Pat. No. 6,322,502, which is an application filed pursuant to 35 U.S.C. §371 based on International Application PCT/IB97/01606 filed on Dec. 29, 1997, and which claims priority benefit of U.S. Provisional Patent Application Ser. No. 60/034,111 filed on Dec. 30, 1996, which are all hereby incorporated by reference.

FIELD OF THE INVENTION

The present invention relates to computerized information systems, and more particularly to information systems which can receive patient data and information from various sources and can display such information in a variety of easily understood formats for use by members of a medical team in a hospital, clinic or office.

BACKGROUND

When an individual is admitted as a patient into a hospital, certain information about the patient must be acquired and made available to various members of the hospital staff. Such information includes, for example, the patient's identity, address, age and occupation, next of kin, medical history, conditions for which treatment is sought, preexisting conditions, and any medical insurance information.

During a patient's stay in a hospital, written information relating to his medical history, doctors' and nurses' observations and remarks, laboratory reports, diagnoses, doctors' orders, prescriptions and other notes by the medical team, including doctors, nurses, technicians, orderlies and the like, become part of the patient's file. Patients with chronic conditions or who are frequently hospitalized may have numerous files of substantial size which contain important historic, as well as current, information. The information that is necessary to provide a complete picture of the patient includes, for example, the patient's vital signs, fluid balance, respiratory function, blood parameters, electrocardiograms, x-rays, CT scans, MRI data, laboratory test results, diagnoses, prognoses, evaluations, admission and discharge notes, and patient registration information. This information originates from a variety of sources, including the patient, doctors, nurses, monitors connected to the patient, testing laboratories, the patient's medical records, and hospital administration records.

A massive amount of information about the patient is therefore generated in a relatively short time. Some or all of this information is typically manually recorded in a flowchart which is affixed to the patient's bed. A disadvantage of manual recordation of such information is that it is slow and tedious. Consequently, such information is susceptible to later misinterpretation because of illegibility, incompleteness, the sheer volume of information being recorded and tracked, and human error.

Although critical care environments, such as hospital intensive care units, trauma units, emergency rooms and the like, are filled with state-of-the-art electronic equipment for monitoring of patients, these devices still do not provide the medical team with a clear and complete picture of the patient and the efficiency of the treatment which he is receiving.

Existing medical display systems are disadvantageous because they are incapable of interconnection with a variety of instruments and monitors, especially if such equipment is made by several different manufacturers. In addition, most existing systems save patient data for a relatively short time, often for less than the duration of a typical patient's stay in the hospital. Also, existing systems typically cannot accept the manual entry of information and/or cannot combine such information with data received from other electronic devices.

Much of the information contained in a patient's files may be absolutely essential for effective and timely treatment. Unfortunately, this essential information may not be easily retrievable from the volumes of information in a patient's records. The necessary information may be overlooked, or mistranscribed, or entered in an incorrect location on the chart. In other circumstances, because of the urgency associated with the patient's condition, the medical team may not have time to search through a patient's file for certain vital information.

In addition, a patient's treatment plan consists of a series of instructions that may change during the course of treatment. In a manually recorded and displayed system, such as a flowchart attached to a patient's bed, it is difficult to ensure that all details of a treatment plan are recorded, and it is difficult to track such manually recorded information. As a result, a patient may receive a treatment late, or not at all. Clearly, if the medical team cannot access essential information about a patient in a timely and complete manner, the quality and effectiveness of the care and treatment of the patient may be compromised.

Many hospitals have changed the way in which patients are billed for services. In the past, patients were typically billed on the basis of days hospitalized. With recent changes in health care management and practice, patients are now more likely to be billed on the basis of treatments received. Greater efficiency in the treatment of patients is therefore emphasized. As a consequence, hospitals now scrutinize the effect of a treatment on a patient more closely, with increased monitoring, observation and recordation of the patient's responses to treatment. The increased amount of information that must be recorded about a patient makes the existing manual-entry system extremely cumbersome and time-consuming for the medical team.

There exists a need for all data and information obtained from and about a patient in a hospital to be immediately and selectively accessible to various members of the medical team in a hospital in accordance with the function performed by those members.

OBJECTS OF THE INVENTION

An object of the present invention is to obviate the disadvantages of the prior art.

Another object of the present invention is to provide a medical information system which displays all types of medical information about a patient in a variety of easily understood formats.

Another object of the present invention is to provide a medical information system which receives patient information from a wide variety of sources, such as, for example, doctors, pharmacists, patient monitoring equipment, testing laboratories, and other computer databases.

Another object of the invention is to provide a medical information system in which access to selected subsets of patient information is gained by selection of specific data sets identified by "job function" selection icons.

Another object of the invention is to provide a medical information system which permits a member of the medical team to record observations about a patient using key words and phrases which can be supplemented with additional text for customized notation.

Another object of the invention is to provide a medical information system which presents multiple types of patient data simultaneously.

Another object of the invention is to provide a medical information system which can be accessed by more than one user and which permits simultaneous viewing of patient information by more than one user.

Another object of the invention is to provide a medical information system which can be updated in real time with additional patient information.

Another object of the invention is to provide a medical information system which permits graphical displays of multiple types of patient data using a common time scale.

Another object of the invention is to provide a medical information system which provides for score computation and identification of missing parameters or values necessary for successful computation.

Another object of the invention is to provide a medical information system which provides for active control of peripheral devices, such as respirators, infusion pumps, intravenous pumps, and the like.

Another object of the invention is to provide a medical information system which is capable of storing patient data for at least the period of the patient's current hospitalization, and preferably for much longer periods of time.

Another object of the invention is to provide a medical information system which is capable of recalling patient data from records created during previous hospital stays.

SUMMARY OF THE INVENTION

These and other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 2A shows an exemplary display screen, illustrating split-screen aspects of the invention;

DETAILED DESCRIPTION OF THE PREFERRED EMBODIMENT

Figure 1:
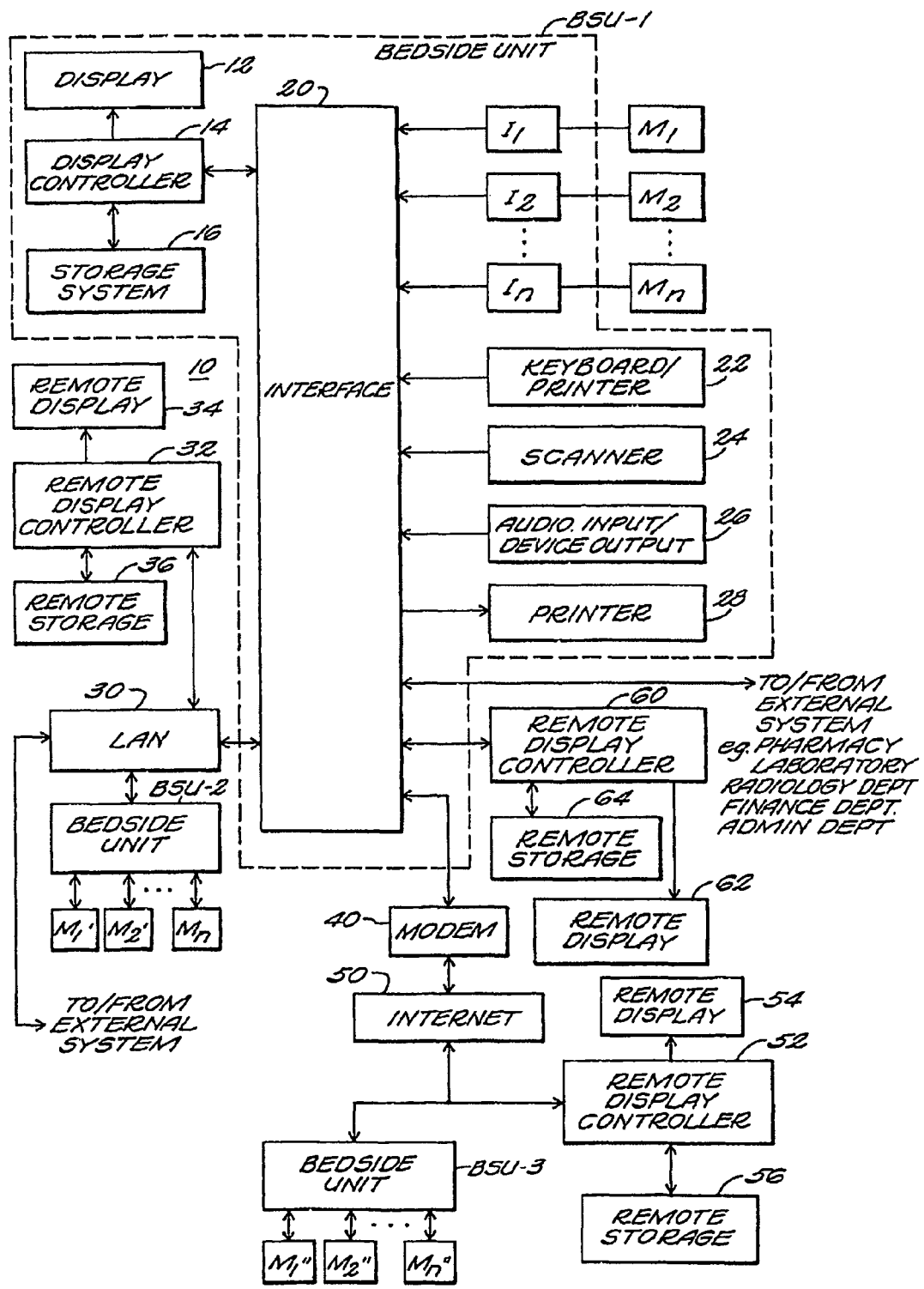
FIG. 1 shows in block diagram form, a medical information system embodying the invention.

A medical information system 10 of the present invention is shown in FIG. 1. The system 10 includes a primary display 12, and an associated display controller 14 and system storage device 16. The controller 14 is coupled to a primary interface nit 20. Keyboard and/or pointing device 22, scanner 24, audio input and/or output device 26 and printer 28 are all coupled by way of interface unit 20 to the display controller 14. In the preferred embodiment, these elements are established by a personal computer such as a Gateway 2000 Pentium Pro™ 200 Mhz system, programmed to perform the functions described in detail below.

A plurality of patient bedside monitors (such as a Hewlett-Packard Model M66 Merlin monitor) and other instruments (such as Puritan-Bennett Model 7200 ventilator), denoted M1, M2, ... $M_n$ in FIG. 1, are coupled by way of separate interface units, I1, I2, ... , $I_n$ respectively, to the display controller 14.

In the illustrated embodiment, the various units M1, M2, ... $M_n$, and their associated interface units I1, I2, ... $I_n$, as described in detail below. Together, elements 12, 14, 16, 20, I1, I2, ... $I_n$, In establish a bedside unit, denoted BSU-1 in FIG. 1.

In the present embodiment, the interface 20 also is coupled by way of a local area network (LAN) 30 to a remote display controller 32, which in turn is coupled to a remote display 34 and a remote storage 36. In other embodiments, the latter coupling may be effected by way of an interface similar to interface unit 20, which in turn may be coupled to various bedside monitors or other instruments.

The interface unit 20 is also coupled by way of modem 40 and the Internet 50 to another remote display controller 52, which in turn is coupled to a remote display 54 and remote storage 56. In a similar manner, this coupling may be effected by way of another interface similar to interface unit 20, which may also couple various bedside monitors and other instruments.

In addition, the interface unit 20 is also directly coupled to a remote display controller 60, which in turn is coupled to remote display 62 and remote storage 64.

A second bedside unit BSU-2 couples units M1, M2 and $M_n$, (which may be similar to elements M1", M2", and $M_n$") by way of LAN 30 to interface 20.

In BSU-1, the display 12 generates images in response to a set of display signals which are generated by display controller 14. The controller 14 is capable of receiving multiple data sets, each data set being representative of medical information. The controller 14 includes a user device (keyboard/pointer 22) which is responsive to a user selection action for generating a selection signal. The user device may be any kind of selection device, for example, a keyboard (with cursor control), mouse, light pen, trackball, touch pad, or voice controlled pointer provided by speech recognition software.

In the illustrated form of the invention, the selection signal represents one of several subsets of the medical information data sets. Each subset is associated with a user job function or a user department. The number of possible subsets of the medical information data sets is greater than one. The controller 14 is also capable of generating display signals in response to the selection signal. The display signals represent the subset of medical information which is associated with the generated selection signal. The displayed image also corresponds to the subset associated with the generated selection signal.

By way of example, the user job functions are selected from the group consisting of doctor, nurse, pharmacist, administrator, insurance coordinator, quality controller, and assistants thereto. The departments are selected from the group consisting of medical, pharmacy, administration, finance, and insurance departments. In other forms of the invention, additional, or different sub-sets of, user job functions and departments may be incorporated.

The data sets include sets of information from the group consisting of patient identity and admission information, patient diagnosis information, patient measurement information, patient treatment plan information, patient order information, and patient treatment information. Additional, or different sub-sets of, data sets may alternatively be incorporated in other forms of the invention.

As described more fully below, BSU-1 collects data in real time from a variety of sources, including electronic monitoring equipment attached to the patient and in remote laboratories, as well as other input devices, such as a keyboard, by which a member of the medical team can record observations, notes, orders and the like. Each instrument is interconnected with the display system with a universal interface device for facilitating input and output of information, such as, for example, an RS-232 interface. In the present embodiment, BSU-1 includes a Windows-type operating system which provides a user-friendly display screen with prompts for accessing and entering medical information.

The medical data and other information of interest to the medical team is stored in a personal computer (PC), which processes and displays the information in real time in a graphic and/or text display. Various reports can be generated from the stored data. The user can combine different sets of data from different sources to obtain customized summaries of the patient's status and progress.

In use, a BSU is located near each patient bed in a hospital ward, such as in an intensive care unit (ICU). The BSU is coupled to each of the electronic monitoring devices attached to the patient, such as, for example, a respirator, blood pressure monitor, or an electrocardiograph (referred to as M1, M2, ... $M_n$ in FIG. 1). In other forms of the invention, active devices, such as infusion pumps can be coupled to the BSU. In addition, the BSU is connected via interface 20 to a distributed electronic database, which may be generated or maintained by or in conjunction with other departments within the hospital, such as, for example, imaging, hematology, pulmonary, pathology, and various laboratories. The BSU at the patient's bedside receives information continuously from each of the devices and is adapted to permit manual entry of information as well.

Remote data displays (such as displays 34, 52 and 62, or those in BSU-2 and BSU-3, in FIG. 1) are also located at doctors' offices and nurses' stations to permit the medical team to monitor and review patient information and to receive reminders of actions to be taken. Because all information that is generated is stored in a common database, the system permits simultaneous viewing of the information by multiple users.

The system provides for the entry and monitoring of action items, such as, for example, orders for drugs or other treatments. Operational reminders are then generated and transmitted to the medical team. The system further permits entry of confirmatory information by the appropriate member of the team to verify that an order has been carried out. Compliance with orders is tracked as well, and the display screen can indicate an alarm or other warning indicator which notifies the medical team that an order has not yet been carried out.

The system further has the capability of providing customized notations in a patient's file using predefined phrases which can be combined and edited as needed. The use of predefined terminology eliminates the use of highly specialized or confusing vernaculars in the description of a patient's condition.

The system can additionally perform computations relating to the severity of a patient's condition. The system can access stored data according to user-specified formulae to compute a "score" which reflects a relationship between various factors, each factor being weighted appropriately according to its significance as defined in the formula. The system permits the medical team to define and enter formulae for various conditions. In addition, the system indicates an inability to complete a computation if one or more parameters in a given formula is missing. The system indicates which parameters are missing and, if possible, computes a value for the missing parameter using available information.

Alternatively, all data in the system can be saved locally in each BSU in the network. Thus, at least two copies of the data are retained at all times.

In the illustrated embodiment, reliability is enhanced in the following names. Each BSU in a LAN continuously monitors the integrity of its link to a server. In the event of link failure, incoming data is stored locally at the BSU. Otherwise the data is transferred to a server, where it is mirrored to a backup store or another server in real time.

Use of the system in a hospital can effect a significant savings in the time spent by the medical team in reviewing and recording patient information.

The system includes various security provisions to ensure the integrity of the data as it enters the network, and further to ensure that only authorized persons are able to access the information, enter additional information and orders, and change data. For example, each operator's identity is recorded and associated with each action taken. Operator identity can be encoded, for example, with a multi-digit number or an alphanumeric code. Second, certain operations are restricted to certain members of the medical team: for example, only doctors are permitted to access and enter information relating to prescriptions for drugs and treatment therapies. Only pharmacists are permitted to access and enter information relating to the filling of prescriptions. Only nurses and other technicians are permitted to access and enter information relating to administration of drugs and treatments. Third, customized input masks are provided to ensure that the effects of errors or mistakes are not introduced into the system, such as by the entry of incorrect or incompatible information. For example, if a doctor enters a value which is outside a permitted range, an out-of-range message appears, prompting the user to check the value. Such masks cannot be overridden by the medical team and therefore ensure the integrity of the information in the system.

Split Screen Drag and Drop Display

Figure 2A:
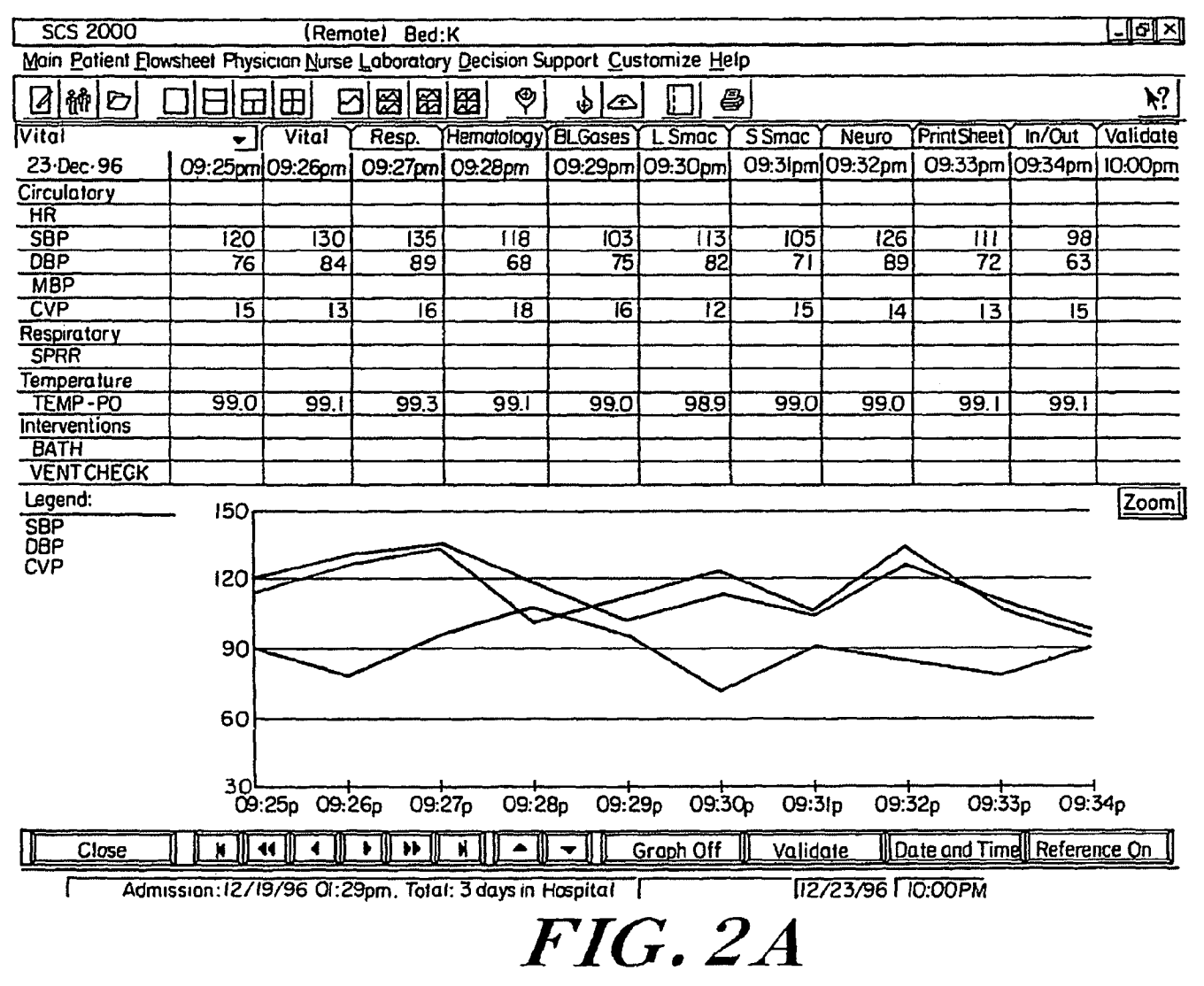

FIG. 2A shows an exemplary screen display showing Vital Signs data for a patient in both tabular and graphical forms. A user may use the graphics "button to select graphic-only, tabular-only, or graphic/tabular (as illustrated) form. When in the latter form, the user can selectively determine which data is graphed by "clicking" on a row of tabular data and "dragging and dropping" that row to the graphic display region, where that tabular data is then illustrated in graphic form on the then-effective time base for the screen. Similarly, to simplify or otherwise customize the graphic display, the user may "click" on one of the graphs and "drag and drop" that graph to the tabular region of the screen, removing that graph from the graphic display region of the screen. Preferably, the different graphs in the graphic display region are different colors, and are coordinated with the colors of the background for the respective legends for the data in the tabular region of the display.

Multiple Image Display

In general, the multiple image display aspect of the invention provides a multiple image medical information system. The display 12 is responsive to display signals for generating n medical data images in an image field, where n is an integer, and where each of the images is in an associated one of n regions of the image field of display 12. A multitasking display controller generates the display signals. That controller includes a data device, a user select device, and a display signal generator. The data device generates patient data representative of patient-related information, including m subsets of the patient data, where m is an integer greater than n. The user select device is responsive to user action to select k of the m subsets of patient data, where k is an integer greater than and less than or equal to n. The display signal generator responsive to the user select device for generating k of the display signals, each being representative of an associated one of the selected subsets of patient data and being associated with one of the regions of the image field. The resultant k medical data images correspond to the k selected subsets of patient data an are displayed on the display 10 in the respective associated regions of the image field. In one form, at least one of the m subsets of patient data is representative of a plot of at least two measured patient characteristics as a function of a reference parameter on a common scale, where the reference parameter is time. Preferably, for one subset of patient data, the measured characteristics and the reference parameters are selectively determined by a user, and wherein the data of at least one of the m subsets of patient data corresponds to measured patient characteristics and associated reference parameter values. The measured patient characteristics may be from the set consisting of blood pressure and others, the associated reference parameters are from the set consisting of time and others.

Figure 2B:
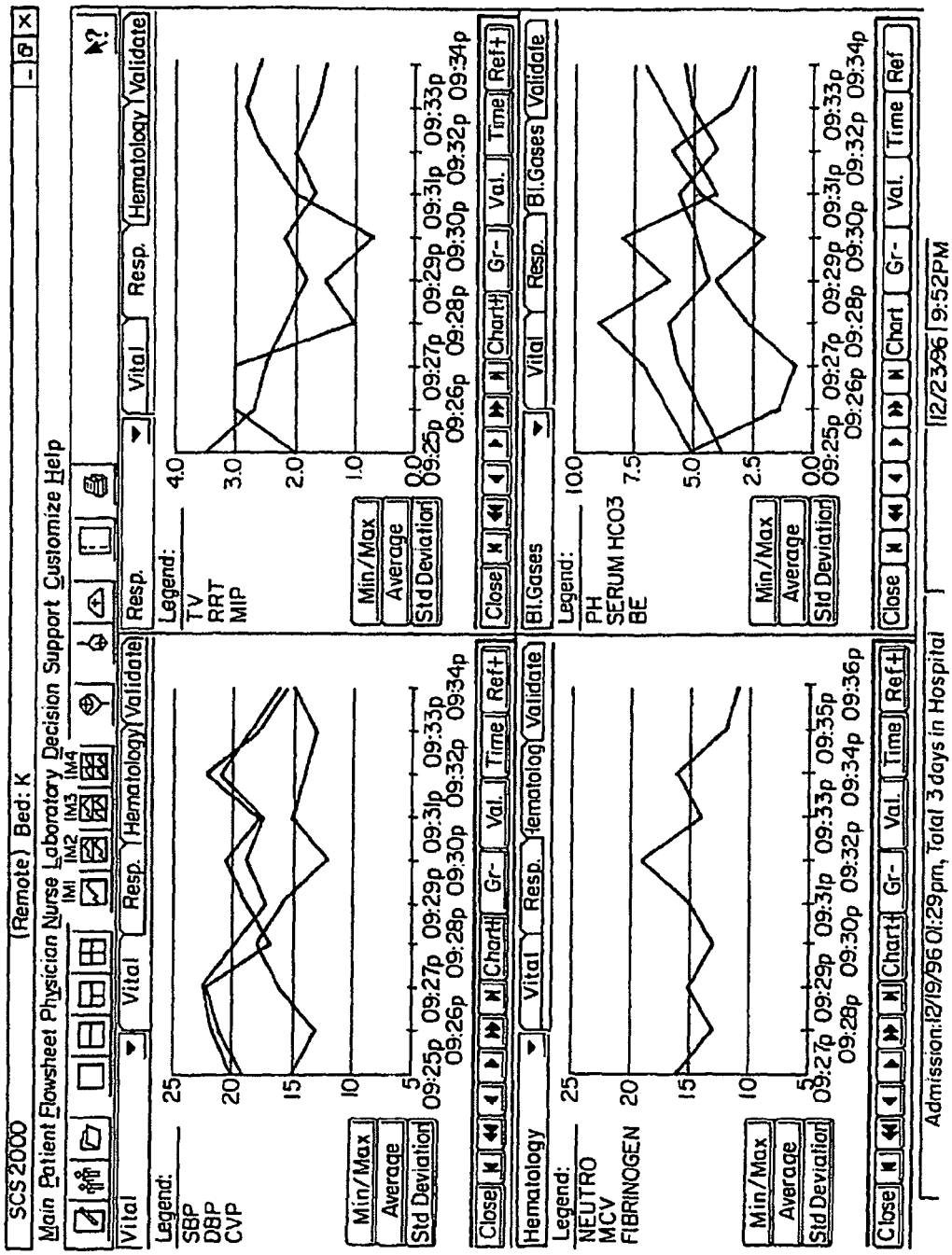
FIG. 2B shows an exemplary display screen illustrating multiple image aspects of the invention.

A screen at display 12, illustrating the ability of the system to present multiple graphical displays of patient information, is shown in FIG. 2B. The menu bar shows icons MI1, MI2, MI3 and MI4 which respectively offer the user a choice of one, two, three or four simultaneous displays. FIG. 2B illustrates four graphical displays entitled VITAL SIGNS, RESPIRATION, HEMATOLOGY and BLOOD GASES. Other displays, such as, for example, FLUID BALANCE, FLUID INPUT and FLUID OUTPUT, or other flow chart parameters, can also be selected. As for the screen display described in conjunction with FIG. 2A, each of the data sets can be displayed in a variety of formats, including graphical, tabular, bar chart and pie chart formats, with or without split screen. As in FIG. 2A, "drag and drop" may be used to modify and/or customize the images. In FIG. 2B, the graph in the VITAL SIGNS display includes multiple traces which represent, respectively, DBP (diastolic blood pressure), SBP (systolic blood pressure) and CVP (heart rate). The table below the graph includes numerical data in one minute intervals of time. The time scale can be selectively changed by a user for any or all of the images.

The data is presented in a way which maximizes its utility and facilitates its interpretation by the medical team. Note that a display may contain more information than can be seen in a multiple-display window. Each display can be scrolled through independently to review all the information contained therein, or maximized to fill the entire display screen, by selecting the appropriate icons at the right side and bottom of each display.

Information is collected in real time. As a consequence, data collection may occur during the period in which a member of the medical team is reviewing a patient's data file. In this instance, a message appears on the display screen to indicate that a particular data set is being updated.

Job Function Display Screen

According to the job function display aspect of the invention, the display 12 is responsive to display signals to generate an image which shows one selected view from a set of possible view of the data in a database at system 10. Preferably, the various possible views are each associated with a job function of a corresponding set of possible system users of system 10. For example, a doctor, by virtue of his or her job function, would generally have an interest in viewing a certain subset of a patient's data from BSU-1. Similarly, a nurse, by virtue of his or her job function, would generally have an interest in viewing a different subset of that same patient's data. FIG. 2A shows an exemplary screen having menu choices for each of a "Physician" and a "Nurse". While not shown in FIG. 2A, other job functions, or department's (such as pharmacy or lab) for whom displays might be desired, can also have menu selectors.

Figure 3A:
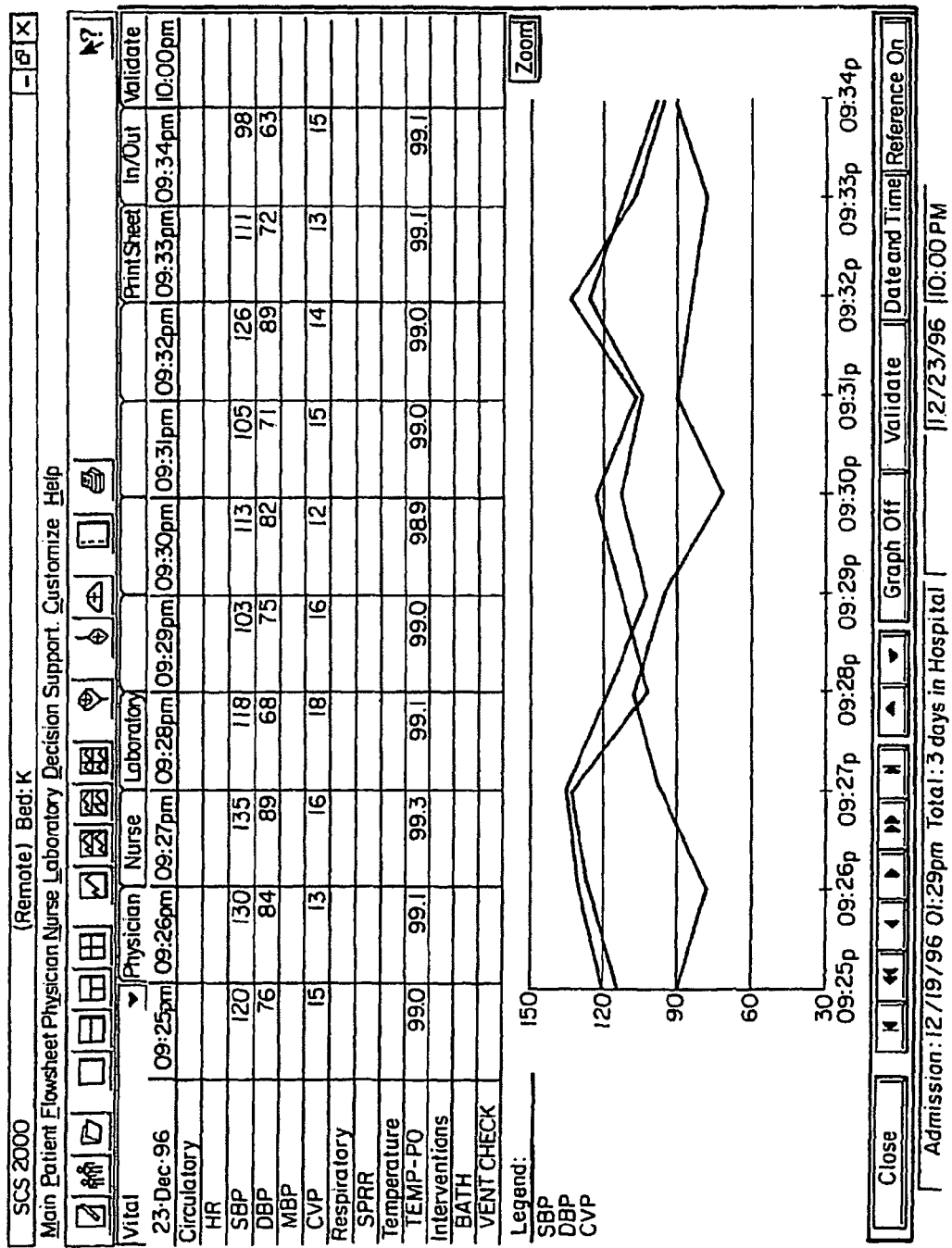
FIG. 3A shows an exemplary "Physician" display screen.
Figure 3B:
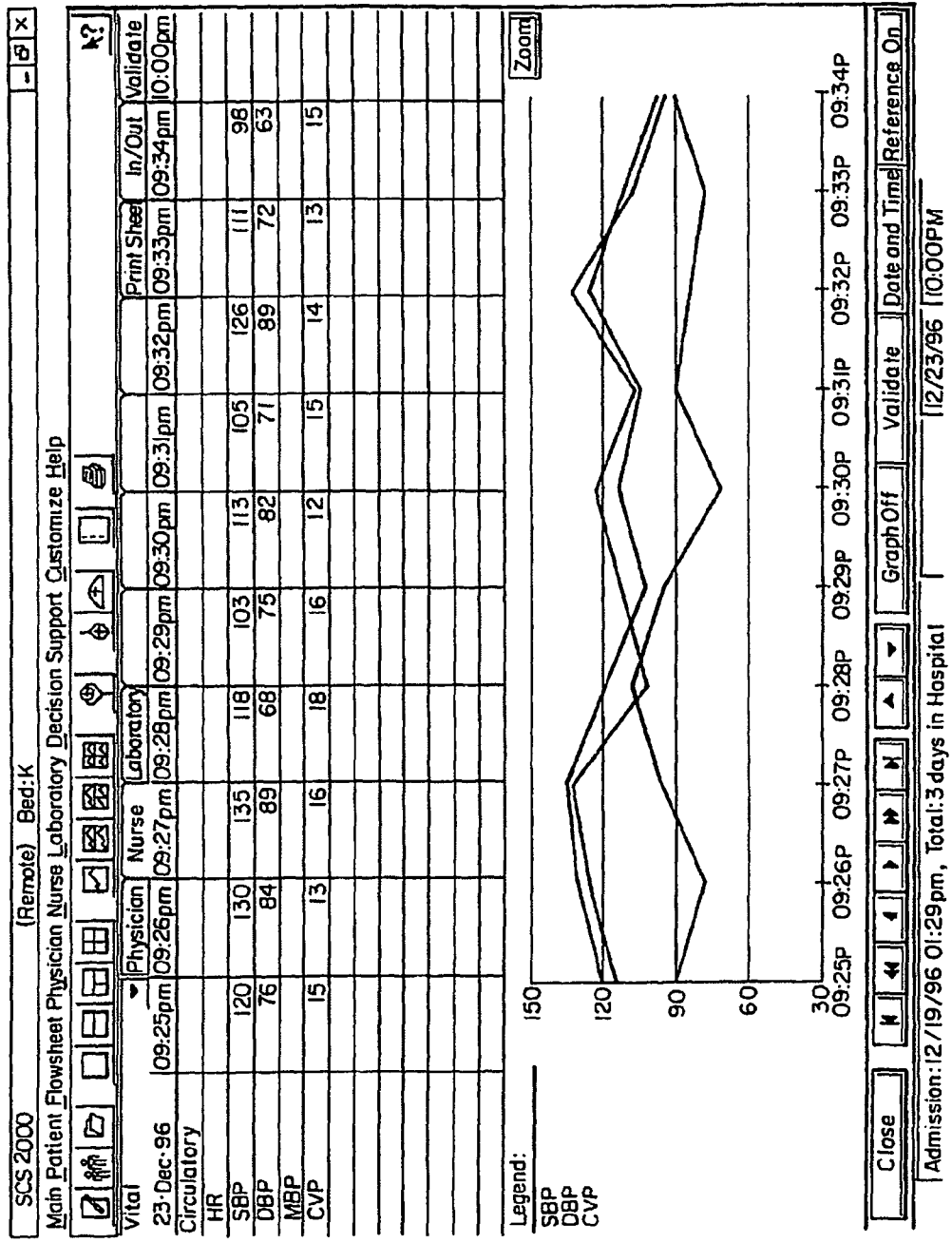
FIG. 3B shows an exemplary "Nurse" display screen.

FIG. 3A is an exemplary screen following selection of "Physician" and FIG. 3B shows an exemplary screen following selection of "Nurse". The screens of FIGS. 3A and 3B show different sets of patient data that may be useful for the Physician and Nurse job functions, respectively. With the invention, each of the data sets for the respective job functions may be custom selected by a user, but in general, because of the difference in needs for users with the different job functions, the displayed data sets will be different.

In operation, the display controller 14 generates the display signals for display 12 in the following manner. Controller 14 receives n sets of data, where n is an integer greater than 1, and where each data set is representative of medical information. A user device 15 responsive to a user action to selectively generate a selection signal representative of one of k subsets of the n data sets, where each of the subsets is associated with one of k user job functions or departments, where k is an integer greater than one. Controller 14 is responsive to the selection signal to generate display signals representative of the subset associated with the generated selection signal, so that the image corresponds to the subset associated with the generated selection signal. By way of example, the user job functions are selected from the group consisting of physician (or doctor), nurse, pharmacist, administrator, insurance coordinator, quality controller, and assistants thereto, and the departments are selected from the group consisting of medical, pharmacy, administration, finance, insurance, epidemiology, human services, and statistical and academic studies departments. The respective ones of the n sets of data include sets representative of information from the group comprising patient identity and admission information, patient diagnosis information patient measurement information, patient treatment plan information, patient order information, patient treatment information.

The following examples illustrate a particular configuration, although many variants can be used within the scope of the invention. Where user job function is "doctor," the k subsets are selected from the group consisting of patient history, physical examination data, current drug data, problem data, orders, progress notes, and summary reports. Where the user job function is "nurse," the k subsets are selected from the group consisting of problem data, care plan, orders, and critical pathways. Where the user job function is pharmacist, the k subsets are selected from the group consisting of drug orders, drug interactions and drug reference data. Where the user job function is administrator, the k subsets are selected from the group consisting of hospitalization days, procedures, and medical staff data. Where the user job functions is insurance coordinator, the k subsets are selected from the group consisting of patient cost data, risk factor data and claim data. Where the user job function is quality controller, the k subsets are selected from the group consisting of procedure time data, staff performance data, and disease/hospitalization data. Where the user department is medical, the k subsets are selected from the group consisting of patient history, physical examination data, current drug data, problem data, orders, progress notes, and summary reports. Where the user department is pharmacy, the k subsets are selected from the group consisting of drug orders, drug interactions and drug reference data. Where the user department is administration, the k subsets are selected from the group consisting of hospitalization days, procedures, and medical staff data. Where the user department is finance, the k subsets are selected from the group consisting of patient cost data, procedure cost data, and staff cost data. When the user department is insurance, the k subsets are selected from the group consisting of patient cost data, procedure cost data, and staff cost data.

In one form of the invention, selection of one of the job function selectors invokes a security program which limits access to a user unless a valid job function related code is and/or personal information number (PIN) is entered. Further, or alternatively, the access control program may control the system to be interactive for one or more users in a first user set and to be read-only for one or more of the selected subsets for one or more users in a second user set. By way of example, the first user set may include only users having the job function of physicians, and the second user set may include only users having the job function of nurse.

Medical Text Display

The medical text display aspect of the invention permits a user to readily compose and store anecdotal information. This is effected by entering text in part via a keyboard or speech recognition device, with a user controlled selector which may be used to select one or more text macro's (or phrases) stored in system 10.

Generally, the display 12 is responsive to display signals for generating text in an image field in display 12. A display controller generates the display signals. That controller includes a memory, a user select device a user text entry device and a display signal generator. The memory includes store data representative of a plurality of discrete phrases, each of the phrases being a sequence of words, or abbreviations or symbols therefore, representative of a medical condition. The user select device is responsive to a user action to (a) display one or more of the plurality of discrete phrases, and (b) select a sequence of one or more of the said phrases and identify text entry points representative of desired positions of the phrases in the image field of display 12. The user text entry device is responsive to user action to selectively determine text to be deleted from the selected sequence of phrases and additional text to be displayed in the image field at desired positions in the image field in or between the selected phrases. The display signal generator is responsive to the select device and the text entry device for generating the display signals, where the display signals are representative of the selected phrases and the determined text at their respective desired positions in the image field. The user select device may be one a keyboard, lightpen, mouse, trackball, touchpad and speech recognition text generator.

Patient Treatment and Progress Monitor

The system 10 also effects planning of patient treatment and monitoring of patient progress. The display 12 is responsive to display signals to generate text in an image field, where that text is constructed to define a treatment plan for a patient. For this function, the system 10 uses display controller 14 and storage system 16. The storage system (or memory) 16 stores (i) problem data representative of one or more possible problems associatable with a patient, (ii) treatment goal data representative of one or more treatment goals associated with each of the possible problems, (iii) treatment plan data representative of one or more treatment plans associated with each of the possible problems, and (iv) patient data. The patient data is representative of the identity of the patient, one or more unresolved problems associated with the patient (where each of the unresolved problems corresponds to one or more of the possible problems) and zero, one, or more of the treatments associated with each of the unresolved problems. The display controller generates the display signals using a user screen entry device which is selectively responsive to user action to (i) generate a display signal representative of the identity of a patient for whom treatment and progress information is to be displayed, and (ii) generate a display signal representative of selected problem data corresponding to the unresolved problems for the patient, treatment goal data associated with the selected problem data for the patient, and treatment plan data associated with the selected problem data for the patient. In one form of the invention, the memory further includes stored cost data associate with the treatment plan data, where the cost data is representative of the cost of effecting said treatment plans. In this form, the user screen entry device is selectively responsive to user action to generate a display signal representative of the cost of the treatment plan associated with the selected problem data for the patient. The user screen entry device is responsive to user action to generate an order signal indicative of a treatment plan to be effected, and for selectively generating a display signal representative of the order signal.

Medical Order Display

The system 10 also provides a display of medical order information. That portion of the system 10 includes the display 12 storage system 16, display controller 14 and an order device. The display 12 is responsive to signals from controller 14 to generate a medical data image. The storage system 16 stores data representative of patient orders. The order device is responsive to user action to generate and store order data in the storage device, where the order data is representative of patient orders. That order data for a patient includes: (i) order data representative of the identity of the prescriber of a prescription, (ii) i.d. data representative of the identification of said patient, (iii) drug data representative of a drug prescribed for a patient in accordance with the prescription, and administration data representative of prescribed dosage and administration times in accordance with the prescription. The display controller generates the display signals. That controller is selectively operative to generate the display signals wherein at least information representative of the i.d. data, the drug data, and the administration data is displayed on said display device. The controller is also selectively operative responsive to user action to generate and store in the storage system, action data representative of an action taken with respect to the patient and one of said prescriptions, where the action data for one of the prescriptions is representative: (a) the delivery of a drug to the patient, (b) the identify of the drug delivered to the patient, and (c) the does and time of the drug delivered to the patient. The controller further monitors the order data for one or more of the patients and detects when action data does not correspond correct fulfillment of the order data and in response thereto, generates a display signal representative of an alarm. In conjunction with the said alarm display signal, an additional alarm may be effected in the form of an audible alarm, a visual alarm or a data alarm. In some form of the invention, the order data further includes authentication data representative of a encrypted identifier uniquely associated with the prescription, and the user device requires a user to generate an access request associated with the authentification data for a selected one of the prescriptions. In this form of the invention, the display generator confirms that the access request corresponds to the authentification data for the prescription and upon such confirmation, enables the user device to modify the data for said patient, modification of the order data is prevented it he event such confirmation is not made.

Medical Information Calculator

The system 10 also provides an improved on-screen medical calculator which permits interactive control by a user to perform computations necessary for various medical treatments and/or decisions. The calculator function permits determination of values from data required by a BSU from various coupled monitors. Where a requested value being determined cannot initially be accomplished for data presently on hand, the system 10 generates a display so advising the user, and also provides a second level routine that permits computation, or user entry, of values for the "missing" data. The latter routine may be selectively performed to generate the necessary intermediate values. In the event data is to present for the second level routine, a similar process may be performed for a third level routine, and so on. Thus, system 10 provides an "intelligent" computations facility.

In general, the calculator function is performed for a BSU with the display 12, display controller 14 and storage system 16. The display 12 is responsive to display signals to generate a medical data image. The display controller 14 generates those display signals. The controller includes storage for sorting (a) at least two primary level computer programs for selectively effecting the determination of an associated first level intermediate value from a plurality of primary values in accordance with a predetermined relationship between the primary values, wherein at least one of the primary values is representative of a measured parameter of a patient, and (b) zero, one or more intermediate level computer programs for selectively effecting the determination of an associated second level intermediate value from at least one of the first level intermediate values and a primary value representative of a measured parameter of a patient in accordance with a predetermined relationship between the one of the first level intermediate values and the primary values. The controller also includes a first memory for storing the primary values other than those representative of measured patient parameters. The first memory includes data values representing the primary values other than those representative of measured patient parameters. A second memory stores the primary values representative of measures patient values and includes data values representative of fewer than all of the primary values representative of measured patient parameters. A user device is responsive to user actions to generate a request signal representative of a request to display a computed value, where the computed value correspond to a value defined by a combination of the predetermined relationship. A processor is responsive to the request signal to invoke one or more of the primary level programs and zero, one or more of the intermediate level programs to effect the computation of the computed value. The process is operative when all necessary primary values representative of a measured patient parameter are resident in the storage devices, for generating the display signal whereby the computed value is displayed on the display device. The processor also determines occasions when a primary value representative of one of the primary values representative of a measured patient parameter is not resident in the storage device. In response to such determination, the process is to generate a display signal whereby a prompt identifying the non-resident primary value is displayed in the display device. The user can then determine and enter a value to be used for the non-resident value so that the desired calculation can be effected.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

What is claimed is:

1. A system for providing expert critical care simultaneously to a plurality of geographically dispersed intensive care units (ICU's) from a remote location, the system comprising:
   a network;
   a plurality of geographically dispersed ICU's comprising means for monitoring patient data elements from a patient and means for transmitting the monitored patient data elements to a remote command center by the network;
   the remote command center connected to the network and comprising:
   one or more display devices;
   a database, wherein the database comprises stored patient data elements relating to the patient;
   a computerized patient care management system connected to a workstation, wherein the computerized patient care management system is adapted for:
   receiving the monitored patient data elements from the plurality of geographically dispersed ICU's;
   storing the monitored patient data elements in the database;
   applying a rules engine to at least two patient data elements stored in the database;
   displaying at least two patient data elements as a series of values over successive periods of time and displaying an indication from an output of the rules engine on the one or more display devices;
   monitoring the medical condition in the patients and utilizing the output from the rules engine to determine if intervention is warranted; and
   wherein the monitoring and intervention for individual patients in the plurality of geographically dispersed ICU's occurs 24 hours per day 7 days per week.

2. The system of claims 1, wherein one of the at least two patient data elements comprises a physiological data element of the patient and another of the at least two patient data elements comprises a clinical data element of the patient.

3. The system of claims 1, wherein one of the at least two patient data elements comprises a physiological data element of the patient and another of the at least two patient data elements comprises a medication data element of the patient.

4. The system of claim 1, wherein one of the at least two patient data elements comprises a physiological data element of the patient and another of the at least two patient data elements comprises laboratory data element of the patient.

5. The system of claim 1, wherein one of the at least two patient data elements comprises a clinical data element of the patient and another of the at least two patient data elements comprises laboratory data element of the patient.

6. The system of claim 1, wherein one of the at least two patient data elements comprises a physiological data element of the patient and another of the at least two patient data elements comprises a physiological data element of the patient.

7. The system of claim 1 wherein the computerized patient care management system further comprises a data server/data warehouse for storing and analyzing data from the remote command center.

8. The system of claim 1 wherein the computerized patient care management system is further adapted to: receive information relating to a medical condition; apply a decision support algorithm; and provide a response based upon application of the decision support algorithm to the information.

9. The system of claim 1 wherein the plurality of ICU's further comprise means for transmitting video and wherein the patient care management system is further adapted to receive video.

10. The system of claim 1 wherein the plurality of ICU's further comprise means for transmitting audio wherein the patient care management system is further adapted to receive audio.

11. A method for providing expert critical care simultaneously to a plurality of geographically dispersed intensive care units (ICU's) from a remote location comprising:
monitoring patient data elements of patients in a plurality of geographically dispersed ICU's;
communicating over a network the monitored patient data elements to a remote command center, the remote command center comprising a database and a workstation;
storing the monitored patient data elements in the database, wherein the database comprises stored patient data elements;
applying a rules engine to at least two patient data elements stored in the database to monitor the medical condition in the patients;
displaying at least two patient data elements as a series of values over successive periods of time and displaying an indication from an output of the rules engine on one or more display devices; and
utilizing the output from the rules engine to determine if intervention is warranted; and wherein the monitoring and determining if intervention is warranted for individual patient occurs 24 hours per day 7 days per week.

12. The method for providing expert critical care simultaneously to a plurality of geographically dispersed ICUs from a remote location claim of 11 further comprising: storing data from the remote command center in a data server/data warehouse; analyzing the data from the command center; and providing results of the analysis over a second network to the remote command center.

13. The method for providing expert critical care simultaneously to a plurality of geographically dispersed ICUs from a remote location claim of 11 further comprising transmitting video from the critical care site via the network to the remote command center.

14. The method for providing expert critical care simultaneously to a plurality of geographically dispersed ICUs from a remote location claim of 11, wherein applying a rules engine to at least two patient data elements stored in the database to monitor the medical condition in the patients comprises applying a rules engine to a physiological measure and a clinical data element of the patient.

15. The method for providing expert critical care simultaneously to a plurality of geographically dispersed ICUs from a remote location of claim 11, wherein applying a rules engine to at least two patient data elements stored in the database to monitor the medical condition in the patients comprises applying a rules engine to a physiological data element of the patient and to a medication data element of the patient.

16. The method for providing expert critical care simultaneously to a plurality of geographically dispersed ICUs from a remote location of claim 11, wherein applying a rules engine to at least two patient data elements stored in the database to monitor the medical condition in the patients comprises applying a rules engine to a physiological data element of the patient and a laboratory data element of the patient.

17. The method for providing expert critical care simultaneously to a plurality of geographically dispersed ICUs from a remote location of claim 11 wherein applying a rules engine to at least two patient data elements stored in the database to monitor the medical condition in the patients comprises applying a rules engine to a clinical data element of the patient and a laboratory data element of the patient.

18. The method for providing expert critical care simultaneously to a plurality of geographically dispersed ICUs from a remote location of claim 11, wherein applying a rules engine to at least two patient data elements stored in the database to monitor the medical condition in the patients comprises applying a rules engine to two physiological data elements of the patient.

* * * * *

UNITED STATES PATENT AND TRADEMARK OFFICE
CERTIFICATE OF CORRECTION

PATENT NO. : 7,899,683 B2  
APPLICATION NO. : 10/985950  
DATED : March 1, 2011  
INVENTOR(S) : Ido Schoenberg et al.

Page 1 of 1

It is certified that error appears in the above-identified patent and that said Letters Patent is hereby corrected as shown below:

Title Page Col. 1 (Inventors), Line 3-4, Delete "Natanya (IL)" and insert -- Netanya (IL) --

Column 13, Line 9, In Claim 10, after "audio" insert -- and --

Column 13, Line 36, In Claim 12, delete "claim of 11" and insert -- of claim 11 --

Column 14, Line 1, In Claim 13, delete "claim of 11" and insert -- of claim 11 --

Column 14, Line 6, In Claim 14, delete "claim of 11," and insert -- of claim 11, --

Column 14, Line 29, In Claim 17, delete "claim 11" and insert -- claim 11, --

Signed and Sealed this  
Third Day of May, 2011

David J. Kappos  
*Director of the United States Patent and Trademark Office*